(12) United States Patent
Li

(10) Patent No.: US 9,649,257 B2
(45) Date of Patent: May 16, 2017

(54) MEDICINE BOTTLE

(71) Applicant: Boe Technology Group Co., Ltd., Beijing (CN)

(72) Inventor: Hui Li, Beijing (CN)

(73) Assignee: Boe Technology Group Co., Ltd., Beijing (CN)

( * ) Notice: Subject to any disclaimer, the term of this patent is extended or adjusted under 35 U.S.C. 154(b) by 140 days.

(21) Appl. No.: 14/443,687

(22) PCT Filed: Jan. 30, 2015

(86) PCT No.: PCT/CN2015/071981
§ 371 (c)(1),
(2) Date: May 19, 2015

(87) PCT Pub. No.: WO2016/082329
PCT Pub. Date: Jun. 2, 2016

(65) Prior Publication Data
US 2016/0361234 A1    Dec. 15, 2016

(30) Foreign Application Priority Data

Nov. 28, 2014   (CN) .......................... 2014 1 0714629

(51) Int. Cl.
*G08B 21/00*   (2006.01)
*A61J 7/04*    (2006.01)
(Continued)

(52) U.S. Cl.
CPC ............. *A61J 7/0481* (2013.01); *A61J 1/03* (2013.01); *A61J 7/04* (2013.01); *A61J 7/049* (2015.05);
(Continued)

(58) Field of Classification Search
CPC ..................................... A61J 1/00; B65D 1/00
(Continued)

(56) References Cited

U.S. PATENT DOCUMENTS 8,174,370 B1      5/2012  Fulmer-Mason
2007/0272583 A1*  11/2007 Kulkarni ............. G06F 19/3462
                                                      206/528
(Continued)

FOREIGN PATENT DOCUMENTS

CN    202346151    7/2012
CN    202605304    12/2012
(Continued)

OTHER PUBLICATIONS

Office action from Chinese Application No. 201410714629.9 dated Apr. 28, 2016.
(Continued)

*Primary Examiner* — Shirley Lu
(74) *Attorney, Agent, or Firm* — Calfee, Halter & Griswold LLP

(57) ABSTRACT

The present invention discloses a medicine bottle having a bottle body comprising a control module, a storage module and an information prompting module; wherein the storage module is configured to store administration information about a medicine contained inside the bottle body; the control module is configured to send a control signal to the information prompting module in accordance with the administration information stored in the storage module, thereby enabling the information prompting module to remind a user to take the medicine. With the above medicine bottle provided in the embodiment of the present invention for containing medicine, it is possible to effectively remind the user of dosage of the medicine to be taken and time to take the medicine at administration time, which is helpful for a patient to control the administration on time in a proper dosage.

16 Claims, 1 Drawing Sheet

(51) Int. Cl.
*A61J 1/03* (2006.01)
*G06F 19/00* (2011.01)

(52) U.S. Cl.
CPC .......... *A61J 7/0418* (2015.05); *A61J 7/0436* (2015.05); *A61J 7/0472* (2013.01); *G06F 19/3456* (2013.01); *A61J 2200/30* (2013.01); *A61J 2200/74* (2013.01); *A61J 2205/70* (2013.01)

(58) Field of Classification Search
IPC ....................................................... B65D 1/00
See application file for complete search history.

(56) References Cited

U.S. PATENT DOCUMENTS

2009/0051560 A1* 2/2009 Manning ............. G06F 19/3468
340/691.6
2013/0256331 A1* 10/2013 Giraud ............... B65D 83/0409
221/1
2015/0272825 A1* 10/2015 Lim ......................... A61J 1/03
340/5.2

FOREIGN PATENT DOCUMENTS

| CN | 103371913 | 10/2013 |
| CN | 203280764 | 11/2013 |
| CN | 103690372 | 4/2014 |
| CN | 103767871 | 5/2014 |
| CN | 103961264 | 8/2014 |
| CN | 103976874 | 8/2014 |
| CN | 203935415 | 11/2014 |
| JP | 2005204685 | 8/2005 |

OTHER PUBLICATIONS

International Search Report and Written Opinion from PCT/CN15/071981 dated Mar. 27, 2015.

Office action from Chinese Application No. 201410714629.2 dated Apr. 28, 2016.

Office action from Chinese Application No. 201410714629.2 dated Aug. 18, 2016.

Office Action from China Application No. 201410714629.2 dated Dec. 27, 2016.

* cited by examiner

MEDICINE BOTTLE

The present application is the U.S. national phase entry of PCT/CN2015/071981, with an international filing date of Jan. 30, 2015, which claims the benefit of Chinese Patent Application No. 201410714629.2, filed Nov. 28, 2014, the entire disclosures of which are incorporated herein by reference.

FIELD OF THE INVENTION

The present invention relates to the field of medical equipment, and particularly to a medicine bottle.

BACKGROUND ART

According to a report released by the World Health Organization, it has been a global problem that patients do not take medicine periodically as required in the doctor's prescription. It is further pointed out in the report that only half the patients on average take medicine persistently in developed countries, while this proportion is even lower in developing countries. For example, among high blood pressure patients in America, China and Gambia, those who take medicine persistently account for only 50%, 43% and 27% respectively. For a patient, not to take medicine on time in a proper dosage may affect the treatment effect, or even damage the liver functions and hence cause other diseases.

Each patient may have different reasons why he/she does not take medicine on time, e.g., the patient or family members of the patient forget the time to take medicine, or the patient is depressive, or the administration procedures of some therapies are too complicated. Particularly in the case of chronic diseases such as diabetes and high blood pressure, where the patient has to take several kinds of medicines on time in proper dosages, it is indeed somewhat difficult to remember the doses of the medicines to be taken and the administration intervals due to occasional interruption of the normal rhythm of life and work.

At present, a major way of ensuring that the patient takes medicine on time is to give an administration prompt by the family members or cell phone software, but it is not helpful for the patient to control the doses.

SUMMARY OF THE INVENTION

In light of that, embodiments of the present invention provide a medicine bottle to better remind the patient to take medicine on time in a proper dosage.

Accordingly, a medicine bottle provided by the embodiment of the present invention comprises a bottle body that comprises a control module, a storage module and an information prompting module;

The storage module can be configured to store administration information about a medicine contained inside the bottle body;

The control module can be configured to output a control signal to the information prompting module in accordance with the administration information stored in the storage module;

The information prompting module can be configured to output prompting information based on the received control signal outputted by the control module.

In a possible implementation, in the medicine bottle provided by the embodiment of the present invention, the administration information comprises: information about administration time and information about administration dose.

In a possible implementation, in the medicine bottle provided by the embodiment of the present invention, the control module comprises: a timer module and an administration timing reminding module electrically connected with the timer module;

The timer module can be configured to count time in accordance with the information about administration time stored in the storage module, notify the administration timing reminding module at the administration time, and start to count time for next administration time after the administration timing reminding module gives a prompt;

The administration timing reminding module can be configured to, upon receipt of the notification sent by the timer module, convert the information about administration dose stored in the storage module into a corresponding administration reminding signal to the information prompting module.

In a possible implementation, in the medicine bottle provided by the embodiment of the present invention, a weight sensing module electrically connected with the control module is further provided at the bottom of the bottle body;

The weight sensing module can be configured to determine a weight of the medicine inside the bottle body;

The control module can be further configured to determine, according to a weight change of the medicine inside the bottle body determined by the weight sensing module, whether the user has taken medicine in a proper dosage within the administration time.

In a possible implementation, in the medicine bottle provided by the embodiment of the present invention, the control module further comprises: an administration dose detection module electrically connected with the weight sensing module and the administration timing reminding module respectively;

The administration dose detection module can be configured to determine by means of the weight sensing module the weight change of the medicine inside the bottle body within a set time period after the administration timing reminding module sends an administration reminding signal to the information prompting module as compared with before the sending of the administration reminding signal to the information prompting module, and send a signal of erroneous administration dose to the information prompting module when it is determined that the weight change does not comply with the administration dosage.

In a possible implementation, in the medicine bottle provided by the embodiment of the present invention, the control module further comprises: a dose calculation module electrically connected with the weight sensing module, which can be configured to determine by means of the weight sensing module a weight of one pill inside the bottle body when the information prompting module prompts the user to put in one pill, and determine by means of the weight sensing module a weight of all pills inside the bottle body when the information prompting module prompts the user to put in all pills, and determine a total number of pills contained inside the bottle body based on the weight of all pills and the weight of one pill.

In a possible implementation, in the medicine bottle provided by the embodiment of the present invention, the administration dose detection module is further configured to determine by means of the weight sensing module whether the weight of the medicine inside the bottle body is not less than that of one dose before the administration timing reminding module sends an administration reminding signal to the information prompting module, and if yes, send a signal of supplementing medicine doses to the information prompting module.

In a possible implementation, in the medicine bottle provided by the embodiment of the present invention, the administration information stored in the storage module further comprises information about shelf life of the medicine contained inside the bottle body;

The control module further comprises: a medicine expiration warning module;

The timer module can be further configured to count time depending on the information about shelf life stored in the storage module and notify the medicine expiration warning module within N days before expiration of the shelf life; N is an integer greater than or equal to 1;

The medicine expiration warning module can be configured to send a signal of replacing medicine to the information prompting module upon receipt of the notification sent by the timer module.

In a possible implementation, in the medicine bottle provided by the embodiment of the present invention, the administration information stored in the storage module further comprises information about administration conditions of the user;

The control module further comprises: an administration detection module configured to present the information about administration conditions via the information prompting module at a set time depending on the information about the administration conditions of the user stored in the storage module.

In a possible implementation, in the medicine bottle provided by the embodiment of the present invention, the information prompting module comprises any one of or any combination of:

a display screen arranged on an outer surface of the bottle body;

a signal transceiving apparatus arranged on the bottle body and capable of communicating with an external display apparatus;

a voice player arranged on the bottle body.

In a possible implementation, in the medicine bottle provided by the embodiment of the present invention, the display screen is a touch control display screen, the touch control display screen being further configured to receive administration information inputted in a touch control manner for the storage module.

In a possible implementation, in the medicine bottle provided by the embodiment of the present invention, the display screen may be a flexible display screen.

In a possible implementation, in the medicine bottle provided by the embodiment of the present invention, the signal transceiving apparatus may be a Blue-tooth apparatus or a WiFi apparatus.

In a possible implementation, in the medicine bottle provided by the embodiment of the present invention, the bottle body may further comprise a charging interface or a charging power supply powering the storage module, the control module and the information prompting module at the bottom of the bottle body.

In a possible implementation, in the medicine bottle provided by the embodiment of the present invention, the storage module may be mounted pluggably inside the bottle body, or fixed inside the bottle body.

Beneficial effects of the embodiments of the present invention include:

A medicine bottle provided by embodiment of the present invention, on a bottle body of which a control module, a storage module and an information prompting module are arranged, the storage module and the information prompting module being electrically connected with the control module respectively; wherein the storage module can be configured to store administration information about a medicine contained inside the bottle body; the control module can be configured to output a control signal to the information prompting module in accordance with the administration information stored in the storage module, thereby enabling the information prompting module to remind a user to take the medicine. With the above medicine bottle provided by the embodiment of the present invention for containing medicine, it is possible to effectively remind the user of the dose of the medicine to be taken and the time to take the medicine at administration time, which is helpful for the patient to control the administration on time in a proper dosage.

DETAILED DESCRIPTION OF EMBODIMENTS

The specific implementations of the medicine bottle provided by the embodiments of the present invention will be described in detail hereinafter with reference to the figures.

Figure 1:
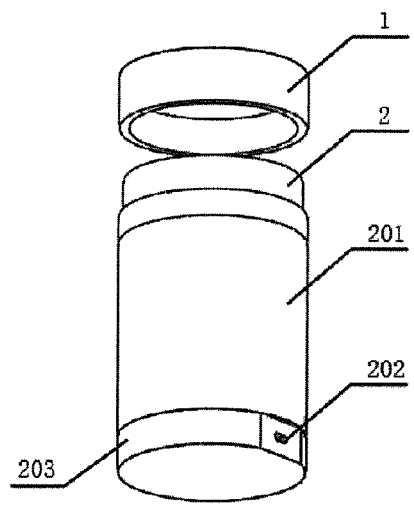
FIG. 1 is a schematic structural view of a medicine bottle provided by an embodiment of the present invention.
Figure 2:
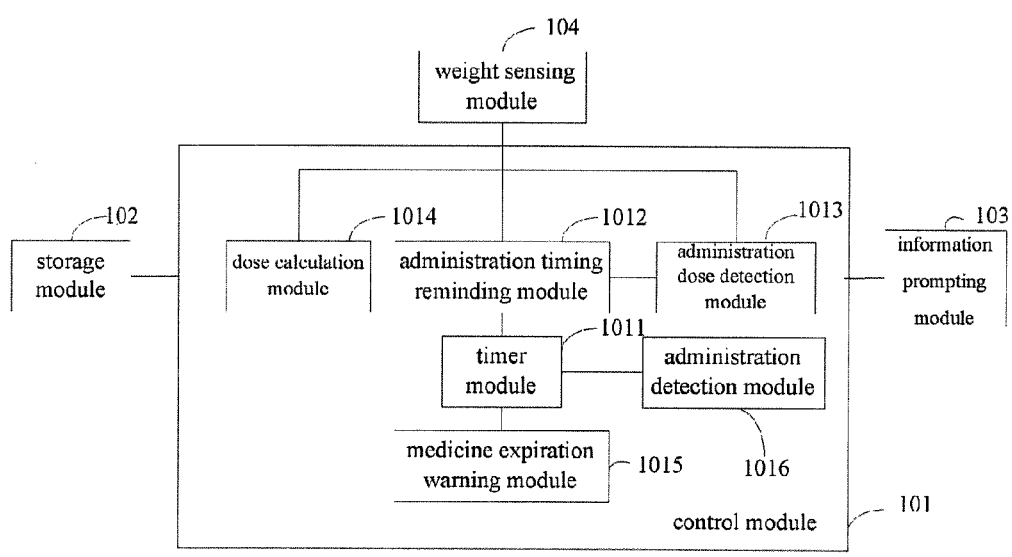
FIG. 2 shows a specific schematic structrual view of a control module in the medicine bottle provided by an embodiment of the present invention.

As shown in FIG. 1, a medicine bottle provided by an embodiment of the present invention comprises a bottle body which may include a cap 1 and a body 2, and as shown in FIG. 2, the bottle body comprises a control module 101, a storage module 102 and an information prompting module 103; wherein, The storage module 102 can be used to store administration information about a medicine contained inside the bottle;

The control module 101 can be used to output a control signal to the information prompting module 103 in accordance with the administration information stored in the storage module 102;

The information prompting module 103 can be used to output prompting information based on the received control signal outputted by the control module 101.

During the specific implementation, the administration information stored in the storage module 102 can comprise information about administration time and information about administration dose, and correspondingly the control module 101 can remind the user at a set administration time to take the medicine in a set dosage via the information prompting module 103.

With the above medicine bottle provided by the embodiment of the present invention for containing medicine, it is possible to effectively remind the user of the dose of the medicine to be taken and the time to take the medicine at the administration time, which is helpful for the patient to control the administration on time in a proper dosage.

During the specific implementation, in the above medicine bottle provided by the embodiment of the present invention, the storage module 102 can be in the form of a memory chip, mounted pluggably inside the bottle body, or fixed directly insided the bottle body. For the first use, the user can either input information about the medicine contained therein such as administration time (including administration intervals) and administration dosage into the storage module 102 via the information prompting module 103, or plug the memory chip out of the bottle body and place it in an editable device for an input, e.g., the memory chip can be disposed in devices such as a cell phone or a computer for edit.

During the specific implementation, the information prompting module 103 in the medicine bottle provided by the embodiment of the present invention can comprise any one or any combination of: a display screen arranged on an outer surface of the bottle body, e.g., a display screen 201 as shown in FIG. 1 can be the information prompting module 103; a signal transceiving apparatus arranged on the bottle body and capable of communicating with an external display device; and a voice player arranged on the bottle body.

The advantage of using a display screen lies in that the user can view the displayed information intuitionally when he/she is reminded to take medicine. Besides, the display screen can be a touch control display screen, with a touch control function of which the user can conveniently input information about the medicine contained therein such as administration time (including administration intervals) and administration dosage into the storage module 102.

Preferably, the display screen can be a flexible display screen mounted on an outer wall of the bottle body for display. Due to its lighter weight, thinner thickness and lower power consumption, a flexible display screen can be helpful for prolonging the service duration of the medicine bottle, and on the other hand it will not occupy too much space.

With a voice player arranged in the bottle body, voice reminding functions can be configured to provide voice prompts to users who have inconveniencies in viewing the screen, e.g., aged people suffering from presbyopia or patients who put the medicine bottle into their bags and forget to get it out.

With a signal transceiving apparatus arranged on the bottle body and capable of communicating with an external display device, the prompting information can be sent to a cell phone of the user or related person in the manner of text message, WeChat or telephone call, so as to facilitate monitoring of the administration by the user or related person. During the specific implementation, the signal transceiving apparatus can be specifically a Bluetooth apparatus or a WiFi apparatus, and so on.

Preferably, it is preferred that the information prompting module 103 in the medicine bottle provided by the embodiment of the present invention comprises all of the above three specific types of information prompting module 103. Descriptions are given as follows by taking an example in which the medicine bottle comprises a flexible display screen, a voice player and a signal transceiving apparatus. However, it should be understood that the present invention is not limited by information prompting modules in these three specific forms. The present invention can also adopt display apparatuses or signal transceiving apparatuses in any other suitable forms as the information prompting module 103.

Furthermore, since some electrical power is required for the control module 101, the storage module 102 and the information prompting module 103 arranged in the above medicine bottle to operate, as shown in FIG. 1, a charging interface 202 or a charging power supply for powering the control module 101, the information prompting module 103 and the storage module 102 can also be arranged at the bottom of the bottle body. In addition, for the convenience of the maintenance of the circuitry, the control module 101 and the storage module 102 can be arranged at the bottom of the bottle body, and thereby a housing 203 at the bottom of the bottle body can be designed in a snap-fit type to prevent water on the one hand, and to facilitate disassembly on the other hand.

During the specific implementation, in order to achieve the function of reminding the user to take a proper dose of the medicine via the information prompting module 103, as shown in FIG. 2, the control module 101 in the above medicine bottle provided by the embodiment of the presnet invention can comprise: a timer module 1011 and an administration timing reminding module 1012 electrically connected with the timer module 1011; wherein, The timer module 1011 can be configured to count time based on the information about administration time stored in the storage module 102, and notify the administration timing reminding module 1012 at the administration time, and start to count time for next administration after the administration timing reminding module 1012 gives a prompt;

The administration timing reminding module 1012 can be configured to, upon receipt of the notification sent by the timer module, convert the information about administration dosage stored in the storage module 102 into a corresponding administration reminding signal to the information prompting module 103. For example, a flexible display screen can be configured to display the dosage of the medicine to be taken, along with a voice prompt that reminds the patient of the administration. Administration prompts can also be sent to a cell phone of a family member of the patient by means of e.g., text message.

Furthermore, in the above medicine bottle provided by the embodiment of the present invention, in order to help monitor whether dose of the medicine for the user is proper, as shown in FIG. 2, a weight sensing module 104 electrically connected with the control module 101 can be further arranged at the bottom of the bottle body, wherein the weight sensing module 104 can be mounted uppermost at the bottom of the bottle body so as to accurately weigh the medicine; the weight sensing module 104 can be configured to determine a weight of the medicine inside the medicine bottle;

The control module 101 may also be configured to determine, according to a weight change of the medicine inside the bottle body determined by the weight sensing module 104, whether the user has taken medicine in a proper dosage within the administration time.

Specifically, in order to achieve the function of monitoring the dose of the medicine taken by the user, as shown in FIG. 2, the control module 101 can further comprise: an administration dose detection module 1013 electrically connected with the weight sensing module 104 and the administration timing reminding module 1012 respectively; the administration dose detection module 1013 can be configured to determine by means of the weight sensing module 104 the weight change of the medicine inside the bottle body within a set time period after the administration timing reminding module 1012 sends an administration reminding signal to the information prompting module 103 as compared with before the sending of the administration reminding signal to the information prompting module 103, and send a signal of erroneous administration dose to the information prompting module 103 when it is determined that the weight change does not comply with the administration dosage, thereby enabling the information prompting module 103 to warn the user accordingly. For instance, the administration timing reminding module 1012 reminds via the information prompting module 103 the user to take three pills at three o'clock, and half an hour later the weight sensing module 104 determines that the weight change of the medicine inside the bottle body is the weight of two pills. Now, the administration dose detection module 1013 needs to send via the information prompting module 103 information about erroneous administration dose to the user such that the patient or family members of the patient can adjust the administration.

Furthermore, in order to facilitate the conversion of the weight change of the medicine into corresponding administration dose (i.e., number of pills that have been taken), the control module 101 can further comprise: a dose calculation module 1014 electrically connected with the weight sensing module 104, which may be configured to determine a weight of one pill inside the bottle body by means of the weight sensing module 104 when the information prompting module 103 prompts the user to put in one pill, and determine a weight of all pills inside the bottle body by means of the weight sensing module 104 when the information prompting module 103 prompts the user to put in all pills, and determine a total number of pills contained inside the bottle body based on the weight of all pills and the weight of one pill. The event that the information prompting module 103 prompts the user to put in one pill or all pills can take place for example at the stage of initializing the medicine bottle when the information prompting module 103 may remind the user to put the medicine into the medicine bottle for the first time.

Furthermore, in the control module 101 of the above medicine bottle provided by the embodiment of the present invention, in order to ensure that the user can have sufficient medicine to take, the administration dose detection module 1013 also may be configured to determine by means of the weight sensing module 104 whether the weight of the medicine inside the bottle body is not less than that of one administration dose before the administration timing reminding module 1012 sends an administration reminding signal to the information prompting module 103, and if yes, send a signal of supplementing medicine dose to the information prompting module 103. For example, each administration dose may include three pills, but it is sensed that there are only two pills based on the weight of the medicine inside the bottle body by means of the weight sensing module 104, then in this case it is necessary to inform the user of information about supplementing medicine doses via the information prompting module 103.

Furthermore, in the above medicine bottle provided by the embodiment of the present invention, in order to ensure the validity of the medicine to be taken by the user, the administration information stored in the storage module 102 can further comprise information about a shelf life of the medicine contained inside the bottle body; for example, for the first use, the user can input information about the medicine contained therein such as administration time, administration dosage and the shelf life of the medicine into the storage module 102 via the information prompting module 103. Correspondingly, the control module 101 can further comprise a medicine expiration warning module 1015 electrically connected with the timer module 1011; and the timer module 1011 may further configured to count time depending on the shelf life information stored in the storage module 102 and notify the medicine expiration warning module 1015 within N days before expiration of the shelf life, N being an integer greater than or equal to 1; the medicine expiration warning module 1015 may be configured to send a signal of replacing medicine to the information prompting module 103 upon receipt of the notification sent by the timer module 1011. For example, the shelf life of the medicine inputted by the user is 10 days, with which the medicine system compares the date at the same time each day. When it is found that there are only three days left for the shelf life, a warning of replacing medicine will be sent via the information prompting module 103.

Furthermore, in order to help the user to monitor the administration conditions of the patient, e.g., to help a doctor to know whether the patient has taken medicine on time in a proper dosage, the administration information stored in the storage module 102 in the medicine bottle provided by the embodiment of the present invention can further comprise information about administration conditions of the user, i.e., each administration condition of the user is recorded in the storage module 102. For example, when the weight sensing module 104 monitors that the weight or number of the medicine has changed, the control module 101 can send an instruction to send the value of change in number monitored by the weight sensing module 104 and the time measured by the timer module 1011 to the storage module 102, and accomplish the recording of the administration dose and administration time of the user. The control module 101 can further comprise: an administration detection module 1016 electrically connected with the timer module 1011, which may be configured to present the information about administration conditions via the information prompting module 103 at a set time depending on the information about the administration conditions of the user stored in the storage module 102. For example, it may send to the doctor information about the administration conditions of the patient in the form of text message at a fixed time each week or each month so as to allow the doctor to track the disease.

A medicine bottle is provided by the embodiment of the present invention, the bottle body may comprise a control module, a storage module and an information prompting module; wherein the storage module may be configured to store administration information about a medicine contained inside the bottle body; the control module may be configured to output corresponding information to the information prompting module in accordance with the administration information stored in the storage module, thereby enabling the information prompting module to remind a user to take the medicine. With the above medicine bottle provided by the embodiment of the present invention for containing medicine, it is possible to effectively remind the user of dose of the medicine to be taken and time to take the medicine at administration time, which is helpful for the patient to control the administration on time in a proper dosage.

Apparently, a variety of modifications and variations for the present invention can be made by the skilled person in the art without departing from the spirit and scope of the present invention. Thus if the modifications and variations of the present invention fall within the range of the claims of the present invention and its equivalent techniques, the present invention is also intended to include such modifications and variations.

The invention claimed is:

1. A medicine bottle, comprising:
   a bottle body, wherein the bottle body having a control module, a storage module and an information prompting module;
   wherein the storage module is configured to store administration information about a medicine contained inside the bottle body;

wherein the control module is configured to output a control signal to the information prompting module to act in accordance with the administration information stored in the storage module; and wherein the information prompting module is configured to output prompting information based on the control signal outputted by the control module, wherein the administration information comprises information about administration time and information about administration dosage, wherein the control module comprises a timer module and an administration timing reminding module electrically connected with the timer module;

wherein the timer module is configured to count time in accordance with the information about administration time stored in the storage module, notify the administration timing reminding module at the administration time, and start to count time for next administration time after the administration timing reminding module gives a prompt; and wherein the administration timing reminding module is configured to, upon receipt of the notification sent by the timer module, convert the information about administration dosage stored in the storage module into a corresponding administration reminding signal to the information prompting module, wherein a weight sensing module electrically connected with the control module is further provided at the bottom of the bottle body;

wherein the weight sensing module is configured to determine a weight of the medicine inside the bottle body; and wherein the control module is further configured to determine, according to a weight change of the medicine inside the bottle body determined by the weight sensing module, whether the user has taken the medicine in a proper dosage within the administration time, wherein the control module further comprises an administration dose detection module electrically connected with the weight sensing module and the administration timing reminding module respectively; and wherein the administration dose detection module is configured to determine the weight change of the medicine inside the bottle body within a set time period after the administration timing reminding module sends the administration reminding signal to the information prompting module as compared with before the administration reminding signal is sent to the information prompting module, and send a signal of erroneous administration dose to the information prompting module when it is determined that the weight change does not comply with the administration dosage.

2. The medicine bottle according to claim 1, wherein the control module further comprises a dose calculation module electrically connected with the weight sensing module, which is configured to determine a weight of one pill inside the bottle body by means of the weight sensing module when the information prompting module prompts the user to put in one pill, determine a weight of all pills inside the bottle body by means of the weight sensing module when the information prompting module prompts the user to put in all pills, and determine a total number of pills contained inside the bottle body based on the weight of all pills and the weight of one pill.

3. The medicine bottle according to claim 2, wherein the administration dose detection module is further configured to determine by means of the weight sensing module whether the weight of the medicine inside the bottle body is not less than that of one dose before the administration timing reminding module sends the administration reminding signal to the information prompting module, and if yes, send a signal of supplementing medicine doses to the information prompting module.

4. The medicine bottle according to claim 3, wherein the administration information stored in the storage module further comprises information about a shelf life of the medicine contained inside the bottle body;

wherein the control module further comprises a medicine expiration warning module;

wherein the timer module is further configured to count time depending on the information about the shelf life stored in the storage module and notify the medicine expiration warning module within N days before expiration of the shelf life;

wherein N is an integer greater than or equal to 1; and wherein the medicine expiration warning module is configured to send a signal of replacing medicine to the information prompting module upon receipt of the notification sent by the timer module.

5. The medicine bottle according to claim 2, wherein the information prompting module comprises any one of:
   a display screen arranged on an outer surface of the bottle body;
   a signal transceiving apparatus arranged on the bottle body and capable of communicating with an external display apparatus;
   a voice player arranged on the bottle body or combinations thereof.

6. The medicine bottle according to claim 1, wherein the administration information stored in the storage module further comprises information about administration conditions of the user; and
   wherein the control module further comprises: an administration detection module configured to present the information about administration conditions via the information prompting module at a set time depending on the information about the administration conditions of the user stored in the storage module.

7. The medicine bottle according to claim 1, wherein the information prompting module comprises any one of:
   a display screen arranged on an outer surface of the bottle body;
   a signal transceiving apparatus arranged on the bottle body and capable of communicating with an external display apparatus;
   a voice player arranged on the bottle body or combinations thereof.

8. The medicine bottle according to claim 7, wherein the display screen is a touch control display screen, the touch control display screen being further configured to receive administration information inputted in a touch control manner for the storage module.

9. The medicine bottle according to claim 7, wherein the display screen is a flexible display screen.

10. The medicine bottle according to claim 7, wherein the signal transceiving apparatus is a Blue-tooth apparatus or a WiFi apparatus.

11. The medicine bottle according to claim 1, wherein the information prompting module comprises any one of:
   a display screen arranged on an outer surface of the bottle body;
   a signal transceiving apparatus arranged on the bottle body and capable of communicating with an external display apparatus;

a voice player arranged on the bottle body or combinations thereof.

12. The medicine bottle according to claim 1, wherein the information prompting module comprises any one of:
- a display screen arranged on an outer surface of the bottle body;
- a signal transceiving apparatus arranged on the bottle body and capable of communicating with an external display apparatus;
- a voice player arranged on the bottle body or combinations thereof.

13. The medicine bottle according to claim 1, wherein the information prompting module comprises any one of:
- a display screen arranged on an outer surface of the bottle body;
- a signal transceiving apparatus arranged on the bottle body and capable of communicating with an external display apparatus;
- a voice player arranged on the bottle body or combinations thereof.

14. The medicine bottle according to claim 1, wherein the information prompting module comprises any one of:
- a display screen arranged on an outer surface of the bottle body;
- a signal transceiving apparatus arranged on the bottle body and capable of communicating with an external display apparatus;
- a voice player arranged on the bottle body or combinations thereof.

15. The medicine bottle according to claim 1, wherein the bottle body further comprises a charging interface or a charging power supply at the bottom of the bottle body for powering the control module, the information prompting module and the storage module.

16. The medicine bottle according to claim 1, wherein the storage module is mounted pluggably inside the bottle body, or fixed inside the bottle body.

* * * * *